(12) United States Patent
Brand (10) Patent No.: US 6,380,414 B2
(45) Date of Patent: Apr. 30, 2002

(54) FRESHLY PRECIPITATED CUO AS CATALYST FOR THE TRIALKOXYSILANE SYNTHESIS

(75) Inventor: Alexandra Brand, Darmstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/860,485

(22) Filed: May 21, 2001

(30) Foreign Application Priority Data

May 23, 2000 (DE) .......................... 100 25 367

(51) Int. Cl.[7] ................ C07F 7/08; C07F 7/18
(52) U.S. Cl. ................................. 556/470
(58) Field of Search ....................... 556/470

(56) References Cited

U.S. PATENT DOCUMENTS

| | | | | |
|---|---|---|---|---|
| 3,775,457 A | * | 11/1973 | Muraoka et al. | 556/470 |
| 4,727,173 A | * | 2/1988 | Mendicino | 556/470 |
| 4,762,939 A | * | 8/1988 | Mendicino | 556/470 |
| 4,778,910 A | * | 10/1988 | Stoffer et al. | 556/470 |
| 4,999,446 A | * | 3/1991 | Moody et al. | 556/470 |
| 5,084,590 A | * | 1/1992 | Ritscher et al. | 556/470 |
| 5,103,034 A | * | 4/1992 | Cho et al. | 556/470 |
| 5,362,897 A | * | 11/1994 | Harada et al. | 556/470 |
| 5,527,937 A | * | 6/1996 | Standke et al. | 556/470 |
| 5,728,858 A | * | 3/1998 | Lewis et al. | 556/470 |
| 5,783,720 A | * | 7/1998 | Mendicino et al. | 556/470 |
| 6,166,237 A | * | 12/2000 | Simandan et al. | 556/470 |
| 6,268,432 B1 | * | 7/2001 | Nakata et al. | 556/470 X |

FOREIGN PATENT DOCUMENTS

| | | |
|---|---|---|
| EP | 0 285 133 | 10/1988 |
| JP | 051 707 73 | 7/1993 |
| JP | 060 652 57 | 3/1994 |
| JP | 101 680 84 | 6/1998 |

OTHER PUBLICATIONS

Okamoto et al. "Synthesis of methoxysilanes by the reaction of metalllic silicon with methanol using copper (II) acetate as the catalyst" Catalysts Letters No. 33, (1995) pp. 421–427.

* cited by examiner

*Primary Examiner*—Paul F. Shaver
(74) *Attorney, Agent, or Firm*—Keil & Weinkauf (57) ABSTRACT

Trialkoxysilanes are prepared by reacting silicon metal with an alcohol in an inert solvent in the presence of a copper catalyst by a process in which the copper catalyst contains copper(II) oxide having a BET surface area of $\geq 10$ $m^2/g$. Furthermore, this copper catalyst is used for the preparation of trialkoxysilanes by reacting silicon metal with an alcohol.

10 Claims, 7 Drawing Sheets

FRESHLY PRECIPITATED CUO AS CATALYST FOR THE TRIALKOXYSILANE SYNTHESIS

The present invention relates to a process for the preparation of trialkoxysilanes by reacting silicon metal with an alcohol over a copper catalyst, in particular over copper oxide, and the use of copper oxide in a process for the preparation of trialkoxysilanes.

Trialkoxysilanes, composed of a silicon atom to which three alkoxy groups and a hydrogen atom are bonded, are very reactive and unstable. They therefore undergo numerous reactions, such as additions, copolymerizations, copolycondensations and disproportionation reactions with other organic compounds, and a number of very useful substances being obtained. These in turn are used as starting materials for silane coupling reagents, coating materials or heat-resistant finishes or for obtaining monosilanes in high purity for semiconductor applications.

The trialkoxysilanes can be prepared by the direct action of silicon metal with the corresponding alcohols at from 150 to 500° C. using copper-containing catalysts (direct synthesis). In general, the copper-containing silicon catalyst material is suspended in an inert, liquid reaction medium and reacted at from 150 to 300° C. by passing in liquid or gaseous alcohol to give the desired trialkoxysilanes. Regarding the conversion of silicon metal and the selectivity of the trialkoxysilane relative to the tetraalkoxysilane present as a byproduct, copper(I) chloride has proven to be a particularly suitable catalyst.

M. Okamoto et al., Catalysis Lett. 33 (1995), 421 to 427 relates to an investigation of the reaction of silicon metal with methanol in a silicon fixed-bed reactor over various copper catalysts. The copper catalysts copper(I) oxide, copper(II) oxide, copper(II) acetate, copper(II) formate, copper(II) phthalate, copper(II) oxalate and copper(I) chloride were compared. The highest silicon conversions (88%) and selectivities for trimethoxysilane relative to tetramethoxysilane (98%) were found for copper(I) chloride.

When copper(I) chloride is used, however, hydrochloric acid is formed and necessitates the use of expensive, corrosion-resistant materials for the reactors used. Furthermore, the presence of chloride in the reaction mixture and in the product leads to a reduction in the yield of trialkoxysilane since the secondary reaction of trialkoxysilane with alcohols to give tetraalkoxysilane is catalyzed by chloride. The hydrochloric acid formed when copper(I) chloride is used as a catalyst can, when the alcohol used is methanol, react with the methanol to give methyl chloride and water, with the result that methanol as a starting material is lost for the trialkoxysilane synthesis.

For these reasons, the use of halogen-free catalysts is desirable.

JP-A-05170773 relates to the preparation of trialkoxysilanes by reacting silicon metal with alcohol in the presence of copper alkoxides. Halide-free products are obtained. The selectivity of this reaction is from 91 to 92% but the conversion of silicon is only from 21 to 32.4%.

An increase in the selectivity and in the silicon conversion is achieved in this reaction according to JP-A-06065257 by using a copper alkoxide catalyst in combination with a metal halide. However, the presence of halide in the reaction mixture and in the reaction product has the abovementioned disadvantages.

EP-A-0285133 relates to the preparation of trialkoxysilanes by reacting silicon metal with alcohols, a copper(II) hydroxide catalyst being used. In this reaction, silicon conversions of from about 80 to 90 mol % are achieved and the amount of tetraalkoxysilanes in the reaction mixture is from about 5 to 10 mol %, based on the silicon.

JP-A-10168084 relates to the preparation of trialkoxysilanes by reacting silicon metal and alcohol over a copper(II) oxide catalyst which has a water content of <3000 ppm. In the preparation of triethoxysilane, a trialkoxysilane selectivity coefficient of 85.2 mol % and a silicon conversion of 91% by weight are achieved. However, the low water content of the catalyst used may require a thermal pretreatment of the catalyst and hence an additional reaction step.

It is an object of the present invention to provide a copper catalyst for the trialkoxysilane synthesis, which catalyst permits high selectivity for trialkoxysilane relative to tetraalkoxysilane and high conversions without the presence of halide being necessary, and which is active in the case of water contents of the catalyst in the percent range. Time-consuming preactivation for generating a catalytically active species is to be dispensed with.

We have found that this object is achieved by a process for the preparation of trialkoxysilanes by reacting silicon metal with an alcohol in an inert solvent in the presence of a copper catalyst.

In the novel process, the copper catalyst contains copper (II) oxide having a BET surface area of $\geq 10$ m$^2$/g.

Preferably, the copper(II) oxide used in the novel process has a BET surface area of from 10 to 50, particularly preferably from 20 to 40, m$^2$/g.

The BET surface area was determined according to DIN 66131.

By means of the novel process, high silicon conversions and very good selectivities for trialkoxysilane in relation to tetraalkoxysilane are achieved. In general, silicon conversions at the end of the reaction of >75, preferably from 80 to 90, particularly preferably from 82 to 90, mol % are achieved. The silicon conversion is determined according to the following equation: Si[mol] in the product/amount of silicon used.

The selectivity for trialkoxysilane relative to tetraalkoxysilane is in general greater than 80, preferably from 85 to 90, mol %. The selectivity is determined according to the following equation: trialkoxysilane[mol]/(trialkoxysilane [mol]+tetraalkoxysilane[mol])·100. Activation of the catalyst used according to the invention by reduction or by a thermal treatment at high temperatures is not required.

The water content of the copper(II) oxides used according to the invention may be in general greater than 5% by weight. The water content of the copper(II) oxide catalyst was not found to have any substantial influence on the results of the reaction.

The copper(II) oxide used according to the invention is preferably freshly precipitated copper(II) oxide. Particularly preferably, the freshly precipitated copper(II) oxide essentially comprises acicular platelets having a length of $\leq 200$ nm. Preferably, the acicular platelets have a length of from 20 to 200 nm, particularly preferably from 20 to 100 nm. The particle size was determined by means of transmission electron microscopy (TEM).

The particle size distribution of copper(II) oxide used according to the invention is in general very narrow.

In a preferred embodiment, the freshly precipitated copper(II) oxide is obtained by reaction of copper(II) salts with sodium hydroxide solution, KOH or Ca(OH)$_2$ and subsequent drying, copper(II) oxide being obtained as a mixture with foreign salts.

Foreign salts are to be understood as meaning the salts formed as byproducts in the reaction, corresponding to the copper salts used.

Usually, the copper(II) oxide thus prepared has a foreign salt content of in general from 0 to 20, preferably from 0 to 5, % by weight. The foreign salt generally does not interfere with the reaction of silicon metal with alcohol to give the trialkoxysilane. However, it should be noted that, when the copper(II) salts used are copper chlorides, sodium chloride is obtained as a foreign salt, but usually in very minor amounts, which plays no role with regard to corrosion problems.

Preferably used copper(II) salts are copper(II) chloride, $CuSO_4$, $CuBr_2$, $Cu(NO_3)_2$, copper acetate, $CuCO_3$, $Cu(CN)_2$ and/or basic copper carbonate, copper(II) chloride and $CuSO_4$ being particularly preferred.

It is possible to control the foreign salt content in the copper(II) catalyst used in the novel process by washing the freshly precipitated copper(II) oxide with a suitable solvent before drying the product. Thus, a product essentially free of foreign salt can be obtained by washing the freshly precipitated copper(II) oxide with water and subsequent drying. Essentially free of foreign salt is to be understood as meaning a foreign salt content of $\leq 2$, preferably from 0 to 1, particularly preferably from 0 to 0.5, % by weight, based on copper(II) oxide.

The freshly precipitated copper(II) oxide is generally dried over a period of from 0.5 to 8, preferably from 0.5 to 3, hours, particularly preferably from 0.5 to 1 hour. The temperature during drying is in general from room temperature to 150° C., preferably from 60 to 120° C., particularly preferably from 90 to 110° C. The drying can also be carried out under reduced pressure. However, a copper(II) oxide catalyst which is active in the novel process is also obtained when the drying of the freshly precipitated copper(II) oxide is carried out, after washing of the copper(II) oxide with methanol or with another readily volatile solvent, at room temperature by evaporation of the methanol or of the other readily volatile solvent.

The BET surface area and the particle size of the copper (II) oxide catalysts used according to the invention are dependent on the drying temperature and duration of drying and on the concentration of the solutions used and the feed rate and hence precipitation rate.

Table 1 shows the chloride content, the BET surface area and the crystallite size of freshly precipitated copper(II) oxide catalysts used according to the invention (samples 1 to 3) and of technical-grade, commercial copper oxides (samples 4 and 5).

in situ, which is converted into copper(II) oxide by boiling the solution.

The data in Table 1 show that the freshly precipitated copper(II) oxide used according to the invention has a substantially greater BET surface area than technical-grade, commercial copper(II) oxide. Furthermore, the BET surface area of freshly precipitated copper(II) oxide washed only with methanol and then dried in air at room temperature by evaporating methanol is greater than that of freshly precipitated copper(II) oxide which was dried at 100° C. (samples 2 and 3).

The attached drawing shows, in FIG. 1 to 4, transmission electron micrographs of freshly precipitated copper(II) oxide as used according to the present invention and, in comparison with this, the micrographs of technical-grade, commercial copper(II) oxide. The scale is shown under the respective Figure.

Figure 1:
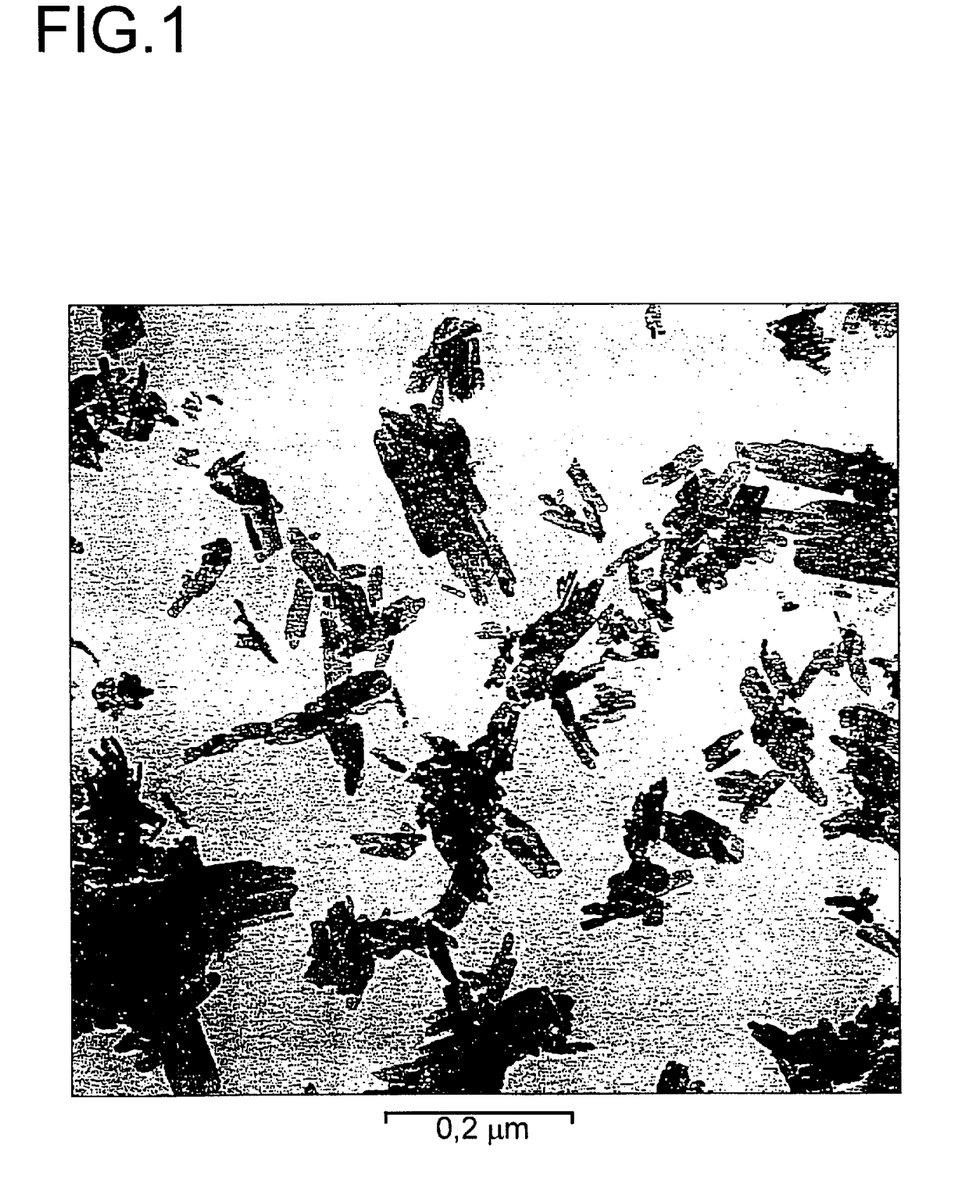
FIG. 1 shows: freshly precipitated copper(II) oxide which was washed with methanol and then dried in air at room temperature by evaporating methanol (sample 1, Table 1)
Figure 2:
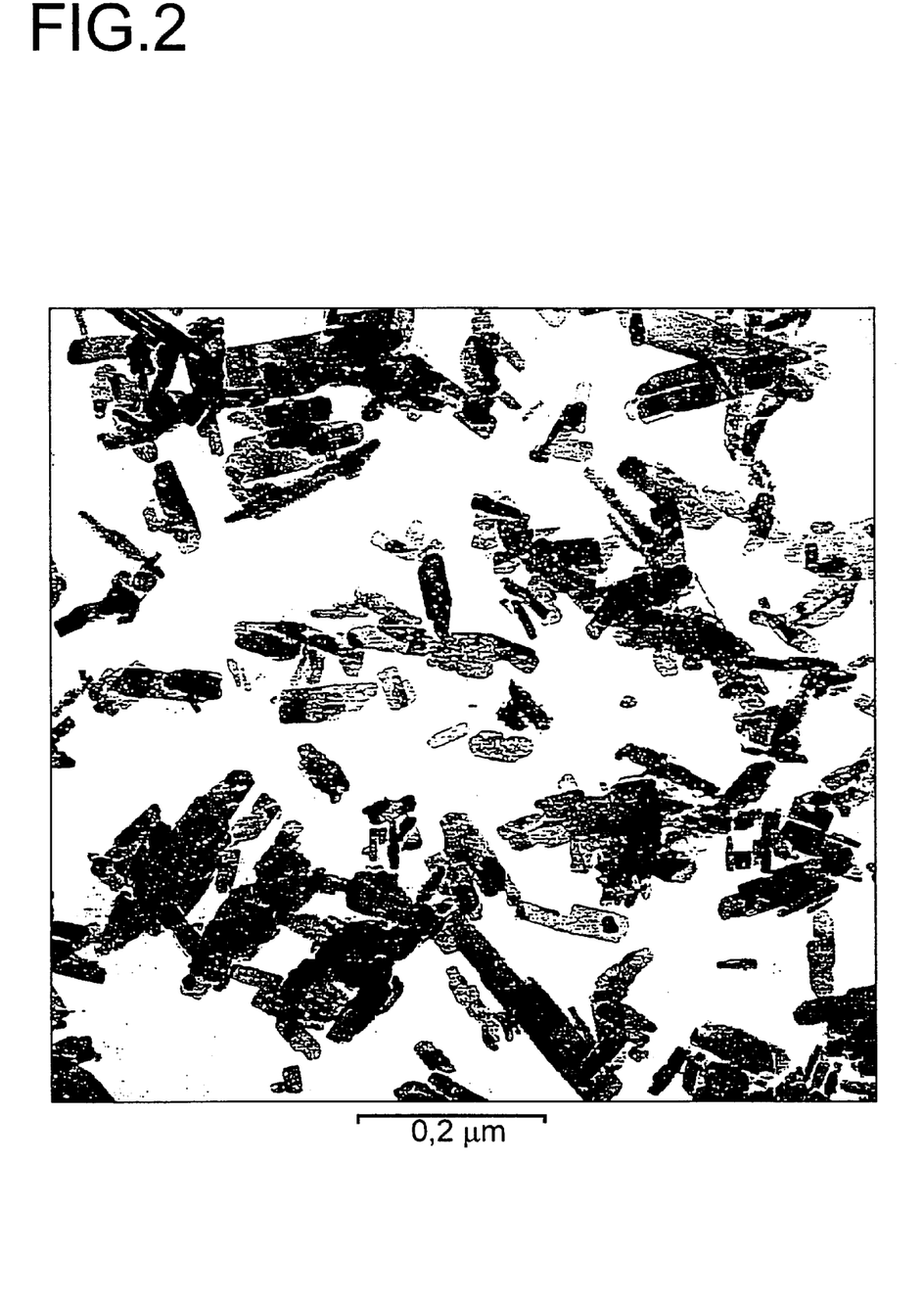
FIG. 2 shows: freshly precipitated copper(II) oxide which was washed with water and dried for 24 h at 100° C. (sample 3, Table 1 ); this copper(II) oxide is essentially halogen-free.

It is evident from FIGS. 1 and 2 that the freshly precipitated salts consist of acicular, flat platelets having dimensions of from 20 to 200 nm. The crystallite size of the sample dried at 100° C. (sample 3, FIG. 2) is on average slightly greater than that of sample 1 (FIG. 1). The total amount of crystalline phases is greater in sample 3 (FIG. 2) than in sample 1 (FIG. 1), also resulting in the larger mean crystallite size.

Figure 3:
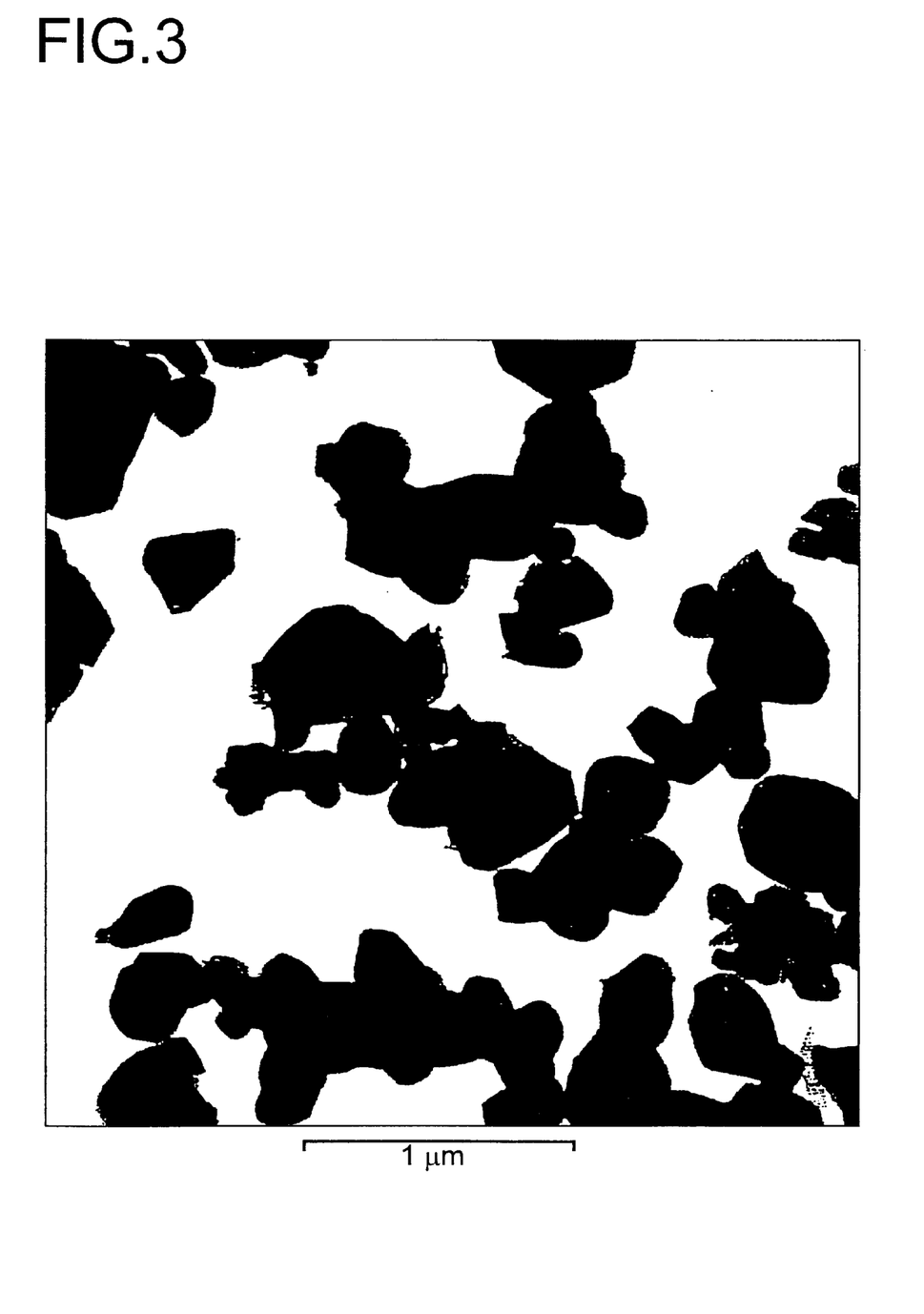
FIG. 3 shows: commercial, granular copper(II) oxide (sample 4, Table 1)
Figure 4:
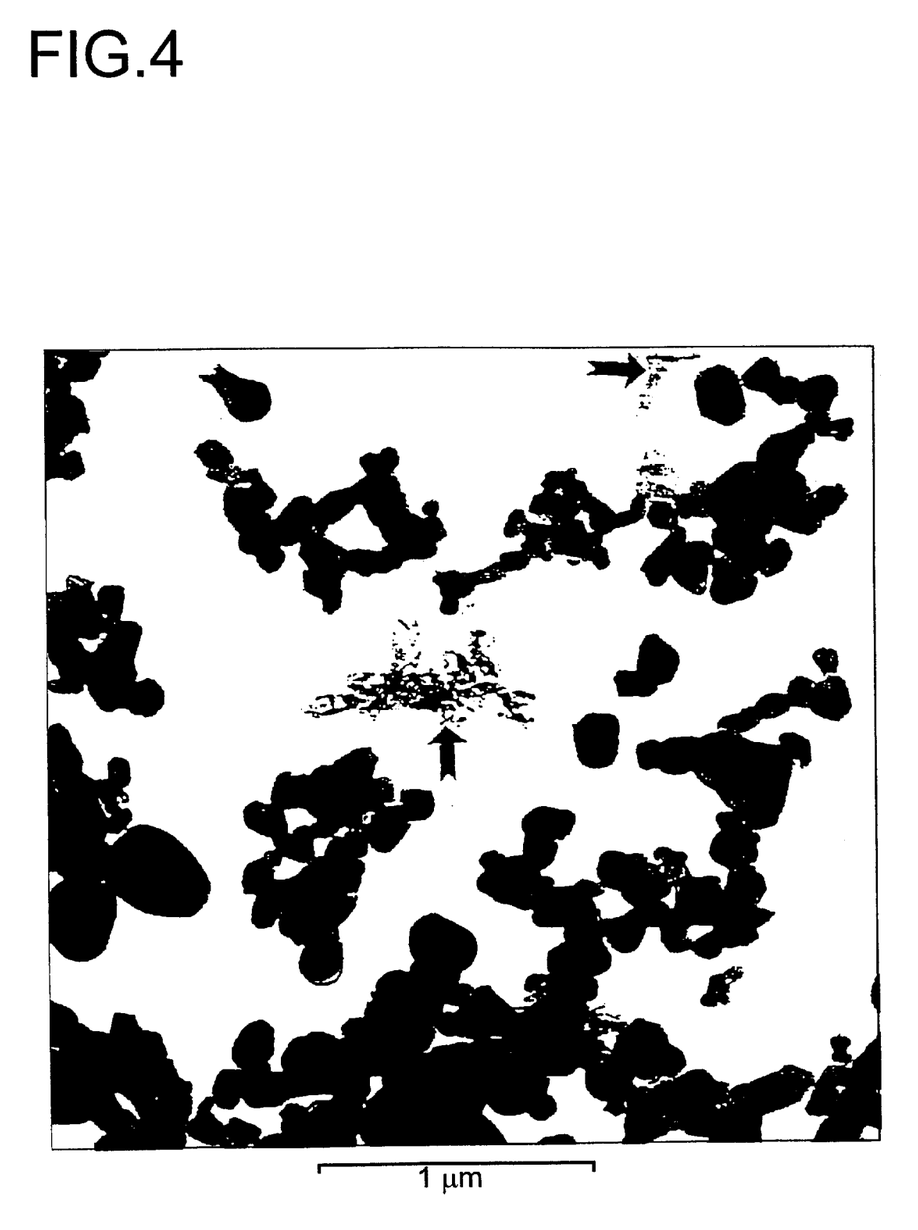
FIG. 4 shows: commercial, powdered copper(II) oxide (sample 5, Table 1).

FIG. 3 and FIG. 4 show that the technical-grade salts have a substantially larger crystallite size of from 20 nm to 9 $\mu$m and a very heterogeneous particle size distribution. The particles are spherical and exhibit a large crystalline fraction. In the powdered sample (sample 5, FIG. 4), acicular fractions which are highly intergrown are additionally found.

In addition to high silicon conversions and a very good selectivity for trialkoxysilane in relation to

TABLE 1

| CuO analyses Sample number | Composition | | | | | | BET surface area | Crystalline | Crystallite sizes |
| --- | --- | --- | --- | --- | --- | --- | --- | --- | --- |
| | Cu | Cl | O | H | Na | Preparation | $m^2/g$ | component | (nm) |
| 1 | 68 | 5.3 | 23.1 | 1.1 | 3.5 | fresh | 36.7 | tenorite, NaCl | 10.5 |
| 2 | 65 | 8.3 | 18.5 | 0.5 | 6.4 | fresh, 24 h, 100° C., $N_2$ | 24.4 | tenorite, NaCl | 13.3 |
| 3 | 76.5 | 0.63 | 21.6 | 0.6 | 0.01 | fresh, washed, 24 h, 100° C. | 25.7 | tenorite | 13.2 |
| 4 | 80 | 0.01 | 19.9 | 0.5 | 0.003 | granular | 2.3 | tenorite | |
| 5 | 80 | 0.5 | 19.2 | 0.5 | 0.003 | powdered | 3.8 | tenorite | |

The technical-grade, commercial copper(II) oxide (tenorite) is usually formed by reacting elemental copper with ammonia, ammonium carbonate and air with subsequent introduction of steam or boiling under superatmospheric pressure with evolution of carbon dioxide and ammonia. However, working-up can also be effected by means of strong alkalis which precipitate copper hydroxide tetraalkoxysilane, the novel process has very good product formation rates.

The amount of copper(II) oxide used in the novel process is variable. In general, from 0.0001 to 0.05, preferably from 0.0005 to 0.005, particularly preferably from 0.001 to 0.005, mol of the catalyst per mole of silicon metal is used.

The alcohol used in the novel process is in general a monohydric alcohol. An alcohol ROH where R is alkyl of 1 to 6 carbon atoms is preferably used. The alkyl group may be branched or straight-chain but is preferably straight-chain. The alkyl group of the alcohol used preferably has from 1 to 3 carbon atoms; particularly preferably methanol or ethanol, very particularly preferably methanol, is used, so that the very particularly preferably prepared product is trimethoxysilane. Usually, the alcohol is passed in liquid or gaseous form into the reaction mixture comprising reaction medium, silicon metal and catalyst.

The alcohol is generally metered continuously in excess into the initially taken silicon metal (i.e. semibatch process). The exact ratio of alcohol to silicon metal depends, inter alia, on the desired method of working up, since it is sometimes necessary to avoid an excessively high methanol content in the product.

The silicon metal used may in principle be any commercially available product. A typical composition of a commercial product, suitable for the novel process, comprises from about >98 to 99% by weight of Si, <1% by weight of Fe, from about 0.005 to 0.7% by weight of Al, from about 0.001 to 0.1% by weight of Ca, <0.001% by weight of Pb and <0.1% by weight of water. Conventional average particle diameters are from 45 to 600 μm, preferably from 75 to 300 μm. In general, small particle diameters of the silicon metal are preferred since they are easier to disperse and react more rapidly.

Inert solvents suitable for the novel process are thermally stable solvents which do not decompose at the high temperatures necessary for the novel process. Preferred solvents are organic solvents which are stable at high temperature and are usually used as heat-exchange media. The type of solvent used considerably influences the reaction of silicon metal with alcohol over copper catalysts. Preferred solvents are Therminol® 59, Therminol® 60, Therminol® 66, Dowtherm® HT, Marlotherm® S, Marlotherm® L, diphenyl ether, biphenyl, terphenyl and alkylated benzenes, alkylated biphenyls and alkylated terphenyls and reaction media which contain diphenylalkanes, as disclosed according to the non-prior-published German application with the file reference 19962571.9. Said solvents have boiling points at atmospheric pressure which are higher than about 250° C. Therminol® 59 is understood as meaning a product from Monsanto Company and (according to the safety data sheet) is a mixture of diphenylethane, ethyldiphenylethane, diethyldiphenylethane and ethylbenzene. Therminol® 60 is a mixture of polyaromatic compounds having an average molecular weight of 250. The optimum temperature of use of Therminol® 60 is from −45 to 315° C. Therminol® 66 and Dowtherm® HT are mixtures of hydrogenated terphenyls having an average molecular weight of 240. Their upper temperature limit is about 370° C. Marlotherm® S, a product from Hüls AG, is a mixture of isomeric dibenzylbenzenes and Marlotherm® L, a product from Hüls AG, is a mixture of isomeric benzyltoluenes. Particularly suitable solvents are Therminol® 59, Therminol® 66, Marlotherm® S, Marlotherm® L and alkylated benzenes, tri- and tetra-toluenes and reaction media which contain diphenylalkanes.

The alkyl chains of the diphenylalkanes generally have a chain length of from 3 to 20, preferably from 10 to 14, carbon atoms. The alkyl chains may be linear or branched. Diphenylalkanes having linear alkyl chains are preferably used. For price reasons, a mixture of diphenylalkanes having alkyl chains of from 10 to 14 carbon atoms is particularly preferably used as the reaction medium.

The amount of solvent used is variable. Usually, for cost reasons, a silicon: solvent composition of from 2:1 to 1:4, preferably from 2:1 to 1:2, is desirable.

A residual content of organic chlorine compounds in the reaction medium has essentially no adverse effect on the reaction. Residual contents of in general from 0 to 10,000 ppm, preferably from 1 to 1000 ppm, particularly preferably from 100 to 500 ppm, based on the reaction medium, may be present in the reaction medium. These organic chlorine compounds do not impart a high degree of corrosiveness to the reaction medium.

Within relatively small limits, the water content of the reaction medium has no effect on the reaction. Water contents of from 0 to 1000 ppm, preferably from 1 to 100 ppm, particularly preferably from 10 to 50 ppm, based on the reaction medium, are usual. Larger amounts of water, which may be introduced, for example, by the alcohol, are however troublesome.

The reaction is carried out in general at from 150 to 300° C., preferably from 180 to 300° C. In some cases, a temperature increase under otherwise identical reaction conditions leads to an improvement in the selectivity, i.e. to an improvement in the ratio of trialkoxysilane to the tetraalkoxysilane formed as undesirable byproduct. The reaction pressure is not critical. Usually, the reaction is carried out at atmospheric pressure.

In an embodiment of the novel process, the inert solvent, the silicon metal and the copper(II) oxide catalyst are introduced into a reactor. The mixture is generally heated to the desired reaction temperature and the alcohol is introduced in liquid or gaseous form into the mixture. After the end of the reaction, the reaction medium can be recovered by filtration and reused. During the reaction, silicon metal is metered in at specific time intervals. Catalysts can be simultaneously metered in. If no catalyst is metered in subsequently, a noncritical, slight decrease in the reactivity of the mixture may be found. In this way, at least ten, preferably from ten to fifteen, times the dose of the silicon metal, relative to the first dose in the reaction medium used, can be reacted.

The present invention furthermore relates to the use of copper(II) oxide having a BET surface area of $\geq 10$ m$^2$/g as a catalyst for the preparation of trialkoxysilanes by reacting silicon metal with an alcohol.

The Examples which follow illustrate the invention.

EXAMPLES

Preparation of Copper(II) Oxide 20 g of copper(I) chloride are initially taken in a 250 ml stirred flask and are dissolved in 26 g of water. 23.8 g of a 50% strength sodium hydroxide solution are rapidly added dropwise. The black suspension is refluxed for 1 hour and filtered with suction. The solid is suspended once in 250 ml of water and filtered off with suction. The residue is then dried for 24 hours at 100° C. under nitrogen. In this way, sample No. 2 (Table 1) is obtained.

If the residue obtained after refluxing is suspended twice in 250 ml of water each time and is filtered off with suction, sample 3 is obtained after the same drying procedure.

Sample 1 is obtained by suspending the residue filtered off with suction in 300 ml of methanol and filtering it off with suction again.

Preparation of Trimethoxysilane
General Method for all Examples Mentioned Below:

500 ml of solvent, 200 g of metallic silicon (average particle diameter 200 μm, silicon content >98%) and about 0.005% by weight, based on the silicon metal, of the copper(II) oxide catalyst are introduced into a 500 ml glass reactor. The reactor is equipped with a thermometer, a condenser, a stirrer and a tube for introducing the alcohol and for introducing nitrogen. The reaction mixture is heated to the reaction temperature stated in Table 2 and liquid methanol is metered in. Shortly after the beginning of the introduction of methanol, the product begins to condense on the condenser. The composition of the product is analyzed by means of gas chromatography.

To permit comparability of the results, balancing was carried out on the basis of a standard reaction time of 22.5 hours. In addition, the balance up to the end of the reaction was also considered (after 23 and 28 hours, methanol content of the product 100%). The reaction discharge consists of a reddish brown suspension, which is filtered. The solvent recovered can be reused.

Figure 5:
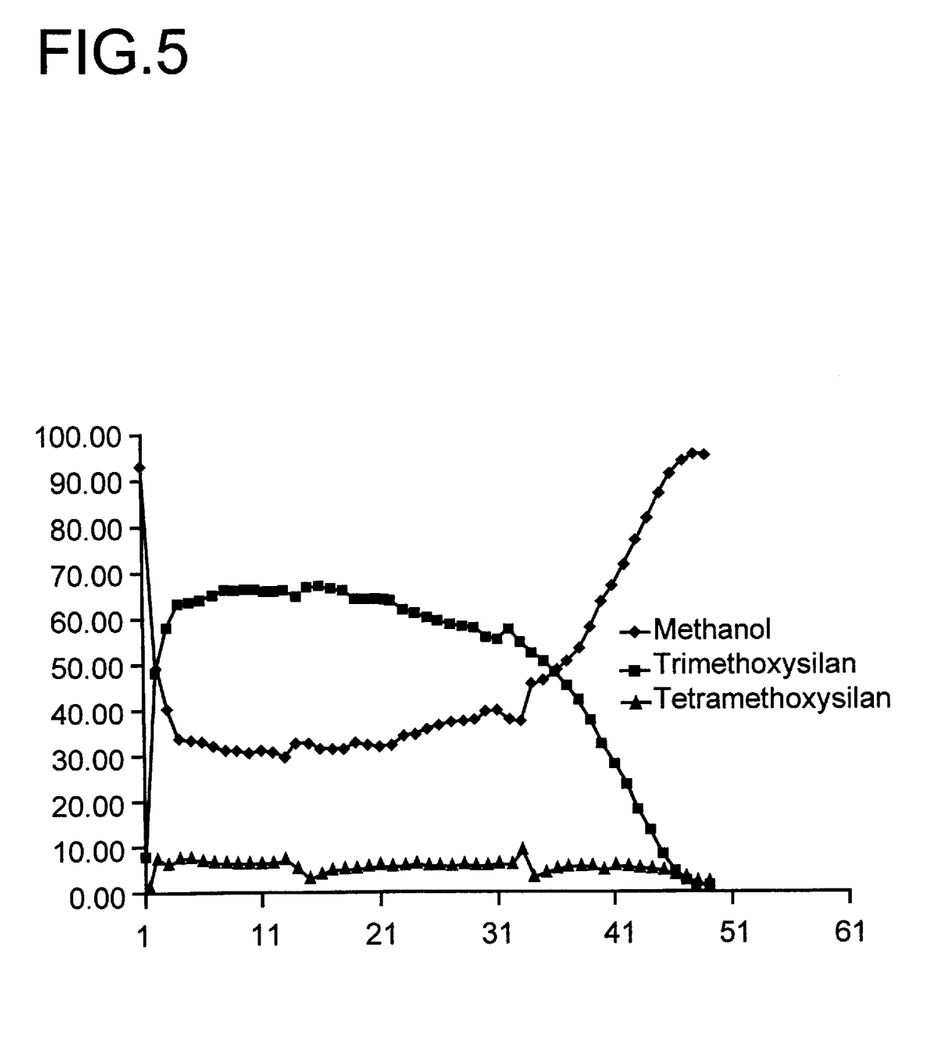
FIG. 5 shows the reaction and product formation rates using a novel copper(II) oxide catalyst, sample 3, Table 1.
Figure 6:
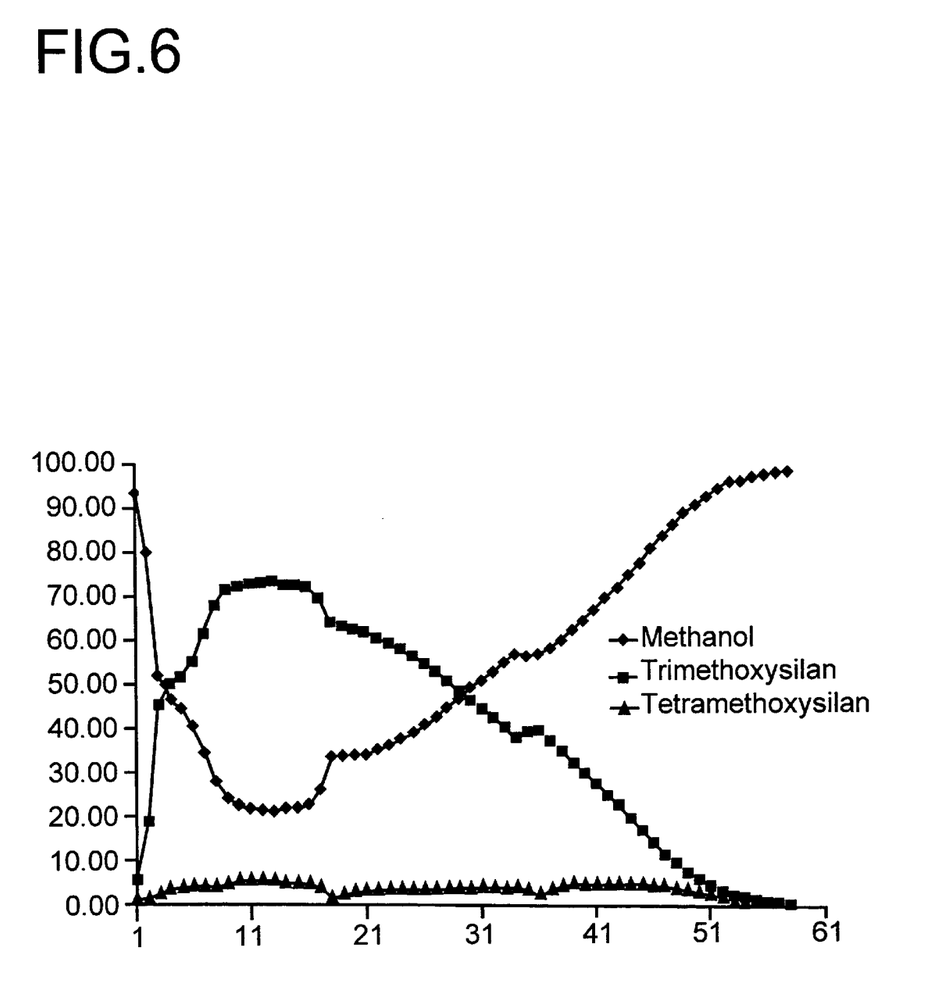
FIG. 6 shows the methanol conversion and the product formation rates using a granular, commercial copper(II) oxide catalyst as a Comparative Example, corresponding to Example 1a according to Table 2.
Figure 7:
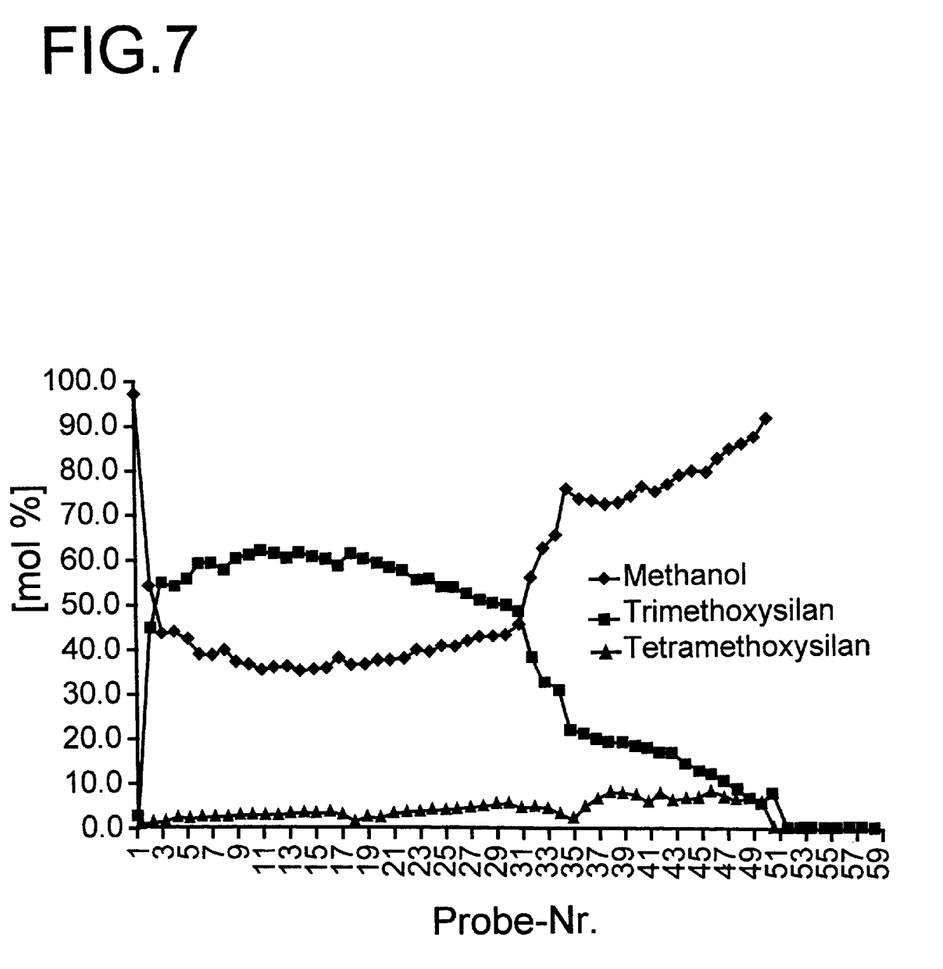
FIG. 7 shows the methanol conversion and the product formation rates using a copper(II) hydroxide catalyst as a Comparative Example according to Example 1b in Table 2.

Table 2 shows the reaction parameters and experimental results of Examples according to the invention and Comparative Examples:

From FIGS. 5 to 7, it is evident that substantially higher product formation rates can be achieved using freshly precipitated copper(II) oxide and using technical-grade copper (II) oxide or copper(II) hydroxide, the selectivities and silicon yields being comparable. No preactivation of the catalyst used according to the invention is required in the reactor. This effect is independent of the solvent used, as shown by Example 2 and Comparative Examples 2a and 2b, according to Table 2.

What is claimed is:

1. A process for the preparation of trialkoxysilanes by reacting silicon metal with an alcohol in an inert solvent in

TABLE 2

| Ex. No. | Temp. (° C.) | Solvent | MeOH throughput (g/minkg$_s$) | Catalyst Type | (g/kgs) | Balance time (h) | Si conversion (%) | Selectivity (TMS/(TMS + TTMS)[mol] (%) | Methanol conversion (%) |
|---|---|---|---|---|---|---|---|---|---|
| 1 | 250 | Marlotherm ® S | 3.07 | CuO[2] (fresh) | 5.35 | 22.5 | 83.0 | 90.21 | 70.25 |
| 1a[1] | 250 | Marlotherm ® S | 3.00 | CuO (granular) | 5.35 | 22.5 | 80.5 | 91.58 | 69.32 |
| 1b[1] | 250 | Marlotherm ® S | 3.10 | Cu(OH)$_2$ | 6.60 | 22.5 | 81.2 | 92.20 | 67.69 |
| 2 | 250 | Wibaryl A | 3.10 | CuO[2] (fresh) | 5.35 | 22.5 | 82.4 | 90.47 | 69.06 |
| 2a[1] | 250 | Wibaryl A | 3.10 | CuO (granular) | 5.35 | 22.5 | 76.7 | 92.80 | 63.67 |
| 2b[1] | 250 | Wibaryl A | 3.07 | Cu(OH)$_2$ | 6.60 | 22.5 | 72.3 | 91.40 | 67.34 |

| Ex. No. | Reaction time (TMS > 1%) (h) | Si conversion (%) | Selectivity TMS/(TMS + TTMS)[mol] (%) | Methanol conversion (%) | Si rate [%/h] | Formation rate TMS [g/h] | Space-time yield, based on catalyst [l/h] |
|---|---|---|---|---|---|---|---|
| 1 | 23.5 | 83.7 | 88.22 | 68.12 | 3.56 | 28.94 | 26.77 |
| 1a[1] | 28.0 | 85.5 | 87.66 | 60.76 | 3.06 | 24.51 | 22.91 |
| 1b[1] | 25.0 | 83.7 | 90.11 | 62.99 | 3.35 | 26.25 | 19.89 |
| 2 | 24.0 | 83.9 | 89.81 | 63.30 | 3.49 | 27.31 | 25.52 |
| 2a[1] | 25.0 | 84.3 | 88.82 | 61.78 | 3.37 | 26.07 | 24.34 |
| 2b[1] | 24.5 | 76.3 | 90.62 | 61.58 | 3.11 | 27.34 | 20.72 |

[1]Comparative Example
[2]Sample 3

In Table 2, the meanings are as follows:

| Ex.: | Example, number of the experiment |
|---|---|
| Temp.: | Reaction temperature in ° C. |
| MeOH throughput: | Throughput of methanol in g per minute and per kg of silicon |
| Catalyst: | Catalyst used and amount of catalyst used in g per kg of silicon |
| Silicon conversion: | Molar amount of silicon in the product per molar amount of silicon used, in percent |
| Selectivity: | Ratio of trimethoxysilane to tetramethoxysilane: trimethoxysilane[mol]/trimethoxysilane[mol] + tetramethoxysilane[mol]) · 100 |

Product Formation Rates Employing a Catalyst Used According to the Invention and Comparative Examples In the attached drawing, FIGS. 5 to 7 show the methanol conversion (rhombuses), the formation rate of trimethoxysilane (squares) and the formation rate of tetramethoxysilane (triangles) in the reaction of silicon metal with alcohols over various halogen-free copper catalysts in Marlotherm® S.

the presence of a copper catalyst, wherein the copper catalyst contains copper(II) oxide having a BET surface area of $\geq 10$ m$^2$/g.

2. A process as claimed in claim 1, wherein the copper(II) oxide has a BET surface area of from 10 to 50 m$^2$/g.

3. A process as claimed in claim 1, wherein the copper(II) oxide is freshly precipitated copper(II) oxide.

4. A process as claimed in claim 1, wherein the copper(II) oxide essentially comprises acicular platelets having a length of $\leq 200$ nm.

5. A process as claimed in claim 3, wherein the freshly precipitated copper(II) oxide is obtained by reaction of copper(II) salts with sodium hydroxide solution and subsequent drying, copper(II) oxide being obtained as a mixture with foreign salts.

6. A process as claimed in claim 5, wherein the foreign salt content of the copper(II) oxide catalyst used can be controlled by washing the freshly precipitated copper(II) oxide with a suitable solvent before drying.

7. A process as claimed in claim 1, wherein an alcohol ROH where R is alkyl of 1 to 6 carbon atoms is used.

8. A process as claimed in claim 7, wherein the alcohol is methanol.

9. A process as claimed in claim 1, wherein the inert solvent is selected from Therminol® 59, Therminol® 66, Marlotherm® S, Marlotherm® L, alkylated benzenes, tri- and tetratoluene and reaction media containing diphenylalkanes.

10. A process as claimed in claim 1, wherein the reaction is carried out at from 150 to 300° C.

* * * * *